United States Patent [19]
Gomberg

[11] Patent Number: 5,440,136
[45] Date of Patent: Aug. 8, 1995

[54] ANISOTROPIC NEUTRON SCATTER METHOD AND APPARATUS

[75] Inventor: Henry J. Gomberg, Ann Arbor, Mich.

[73] Assignee: Penetron, Inc., Ann Arbor, Mich.

[21] Appl. No.: 262,043

[22] Filed: Jun. 17, 1994

[51] Int. Cl.$^6$ .............................................. G01T 3/00
[52] U.S. Cl. ........................ 250/390.04; 250/390.08; 250/391
[58] Field of Search ...................... 250/390.01, 390.04, 250/390.07, 390.08, 391

[56] References Cited

U.S. PATENT DOCUMENTS

| | | | |
|---|---|---|---|
| 4,864,142 | 9/1989 | Gomberg | 250/390.04 |
| 4,918,315 | 4/1990 | Gomberg et al. | 250/390.04 |
| 5,076,993 | 12/1991 | Sawa et al. | 376/159 |
| 5,142,153 | 8/1992 | Gomberg | 250/390.04 |
| 5,247,177 | 9/1993 | Goldberg et al. | 250/390.04 X |

OTHER PUBLICATIONS

Cargo Inspection System Based On Pulsed Fast Neutron Analysis, Brown et al.; *Science Applications Internal Corp;* Santa Clara, Calif. (9/1992), pp. 235–241.

*Primary Examiner*—Constantine Hannaher
*Assistant Examiner*—Edward J. Glick
*Attorney, Agent, or Firm*—Gifford, Krass, Groh, Sprinkle, Patmore, Anderson & Citkowski

[57] ABSTRACT

A non-invasive inspection system employs the isotropic, resonant scattering of neutrons from an object to determine the presence of at least one preselected element therein. A monoenergetic neutron beam is impinged onto the object and a first detector is disposed to detect neutrons resonantly scattered by the preselected element. A second detector is disposed to detect non-resonantly scattered neutrons. Comparison of the signals from the two detectors is indicative of resonant scattering and hence presence of the preselected element.

8 Claims, 5 Drawing Sheets

ANISOTROPIC NEUTRON SCATTER METHOD AND APPARATUS

FIELD OF THE INVENTION

This invention relates generally to methods and apparatus for non-invasively assessing the composition of objects, particularly closed containers or otherwise inaccessible objects. In particular, the invention relates to the use of the anisotropic, resonant scattering of neutrons for determining an object's composition.

BACKGROUND OF THE INVENTION

There exists the need for a rapid, safe, accurate and non-intrusive inspection system for determining the presence of contraband in parcels, luggage, vehicles, and the like, both above and below the surface of the earth. As used specifically herein, contraband shall refer to hazardous materials such as explosives and narcotics, and shall include military explosives such as mines and ammunition. While it is theoretically possible to inspect every parcel or item passed across a border, through an air, rail or sea terminal, or through a post office, such inspection would be very costly, waste time and impede commerce; furthermore, smugglers frequently resort to the use of packages having hidden compartments, false bottoms and the like, which may be overlooked in all but the most scrupulous inspection. There is also a need for explosive detection techniques which may be adapted to scan quickly, the surface or subsurface of the earth for mines or buried explosives. It is preferred that such techniques be reliable, rapid and capable of conducting such inspection from a distance, as for example in a flyover inspection. Accordingly, there is a need for a rapid method for detecting the presence of contraband and it is preferred that the technique be non-invasive or non-visual, that is to say, that it be capable of inspecting the contents of a closed container without necessitating its opening. In many instances a container will not be "closed" in the sense of being sealed, but may be partially opened porous or permeable; however, as used herein, a closed container shall include all such containers not readily subject to visual inspection and shall include parcels, packages and envelopes as well as structural components of buildings and vehicles as well as subsurface or otherwise camouflaged objects.

A variety of techniques have been proposed for accomplishing such inspections. In some instances, thermal neutron activation analysis (TNAA) has been employed. In this technique, relatively low energy neutrons are employed to bombard a sample under investigation. The nuclei of component atoms thereof capture these neutrons and become radioactive. These newly formed radioactive isotopes then undergo gamma decay and emit photons in the process. By identifying the emitted radiation, the composition of the sample may be determined. TNAA techniques are not well suited for the high volume inspection of closed containers since the technique, of necessity, renders the sample being inspected radioactive, and this radioactivity may persist for a significant period of time after completion of the analysis, thereby presenting a potential health hazard. In many instances, the exact composition of the sample under investigation is not known, and consequently the duration of the induced radiation cannot be told beforehand. Furthermore, TNAA techniques are not particularly efficient for detecting nitrogen or carbon, major components of narcotics and explosives, because the capture cross section for these elements is quite small as compared to that of metals and other heavy elements.

In another technique, for example that disclosed in U.S. Pat. No. 5,076,993, an object under investigation is bombarded with fast neutrons having an energy in the range of 5-9 MeV. The neutrons induce the emission of gamma rays from the object and the energy of the emitted gamma rays is correlated with the particular nucleus.

U.S. Pat. Nos. 4,864,142 and 4,918,315, the disclosures of which are both incorporated herein by reference, disclose analytical techniques based upon the elastic scattering of neutrons. The techniques disclosed therein are quite attractive since they do not induce any residual radioactivity in the target elements; also, the elastic scattering cross section for neutrons is much larger than the absorption cross section, and this difference is greatest for the light elements where scattering cross sections are typically 100 to 1,000 times greater than absorption cross sections. Such large cross sections make possible the use of relatively low fluxes of neutrons for scattering analyses. Resonant elastic scattering techniques are of particular interest since they can be highly specific for particular elements. Each element has a unique elastic scattering spectrum characterized by the presence of resonance peaks therein. These resonance peaks represent particular neutron energies at which the elastic scattering cross section of a given element is large. Particular peaks may be correlated with the presence of specific elements.

As detailed in the aforementioned patents, resonance based analyses were heretofore carried out by impinging a monoenergetic neutron beam onto a sample, detecting the elastically scattered neutrons, varying the energy of the monoenergetic beam and making further measurements. A resonance peak will be manifested by a very high scattering cross section, compared to the scattering cross section at other energies. The energy could be varied in a continuous way so as to generate a spectrum; however, in a more practical apparatus, neutron energies of two or more discrete levels were employed to detect specific elements. For example, in order to detect a particular preselected element, a first neutron beam having an energy corresponding to a resonance scattering energy of that element was directed onto the object, and the intensity of elastically scattered neutrons measured. Then, a second beam of neutrons having an energy that will not be resonantly scattered from the preselected element was directed onto the object, and the intensity of scattered neutrons measured. By comparing the two scattering intensities, resonant scattering could be determined. In a practical sense, most objects being investigated will include a number of different elements therein; consequently, the first and second energy levels are chosen so that interference is minimized; i.e., the first energy level is selected so that only the preselected element has a significant resonant scattering thereat, and the second energy level is selected so that none of the elements present in the object has any significant resonant scattering thereat. As is further detailed in the referred-to-patents, the technique may be implemented to determine the presence of multiple elements in an object by selection of the appropriate resonance and reference neutron beams.

It is also possible to determine the relative ratios of preselected elements in an object by using this resonant scatter technique. Various contraband items such as explosives and narcotics have distinct compositions, and the presence of particular elements, such as nitrogen, may be correlated with these items. Furthermore, narcotics, and explosives have rather particular ratios of carbon, oxygen and nitrogen and these ratios may be used to distinguish these materials from one another as well as from ordinary items of commerce, which may also include the aforementioned elements in different proportions.

The monoenergetic neutrons are typically generated by impacting a target material (e.g. D, Li, etc.) with an ionized beam of another material, typically, D or H. By control of the accelerating voltage, the energy of the emitted neutrons may be selected. In many accelerator systems it is somewhat difficult to switch voltage from a first to a second, and back to a first level accurately and quickly. Therefore, in order to simplify the equipment, particularly for field applications, it is desirable to eliminate the need for changing voltage levels and/or neutron energy levels. Furthermore, the sequential impingement of two or more beams of neutrons is time consuming. Consequently, it would be desirable to have a neutron scatter based analysis system in which the need to impinge two neutron beams of different energies onto a sample in sequence is eliminated.

In accord with the present invention, it has been found that the anisotropic nature of the elastic scattering of neutrons may be exploited to simplify the aforedescribed analysis system. It has been found that the intensity of the elastically scattered neutrons exhibits a scattering angle dependence, that is to say the scattered neutrons will produce a strong signal at a first scattering angle and a significantly smaller signal at a second scattering angle. By appropriately selecting the system geometry and the neutron energy, a single neutron beam may be employed to provide both an alarm signal and a non-resonant, reference, signal. In this manner, both the apparatus and methodology for carrying out a non-invasive analysis of objects is greatly simplified. These and other advantages of the invention will be readily apparent from the drawings, discussion and description which follow:

BRIEF DESCRIPTION OF THE INVENTION

There is disclosed herein an apparatus for non-invasive inspection of an object in order to determine the presence of at least one preselected element therein. The apparatus includes a neutron source which generates and directs a monoenergetic beam of neutrons onto the object being inspected. The neutrons generated by the source are of an energy which has been selected such that the neutrons will be anisotropically scattered from the preselected element of interest so as to provide a resonantly scattered group of neutrons at a first scattering angle and a non-resonantly scattered group of neutrons at a second scattering angle. The apparatus includes a first detector which is disposed at a location corresponding to the first scattering angle and a second neutron detector disposed at a location corresponding to the second scattering angle. Each detector is operative to provide a signal corresponding to the neutrons impinging thereupon. The apparatus further includes an analyzer which operates to receive the signal from the first and second detectors and to compare those signals so as to determine if any resonantly scattered neutrons are present. The presence of resonantly scattered neutrons indicates that the preselected element is in the object.

In some instances, the detectors are operative to provide a signal indicative of the intensity of the neutron flux and the system may provide quantitative data. In other embodiments, the analyzer may be further operative to provide an alarm if the preselected element is present. The system may be operative to detect the preselected element in the presence of other potentially interfering elements by selecting the neutron energy and scattering angles so that no resonantly scattered neutrons from the other element will be detected by the first or second detector. The system may further be modified to determine the presence and/or amount of a second element of interest by including a third detector disposed to detect neutrons resonantly scattered from a second element. Also included within the present invention is a method for carrying out the analysis.

DETAILED DESCRIPTION OF THE INVENTION

Figure 1:
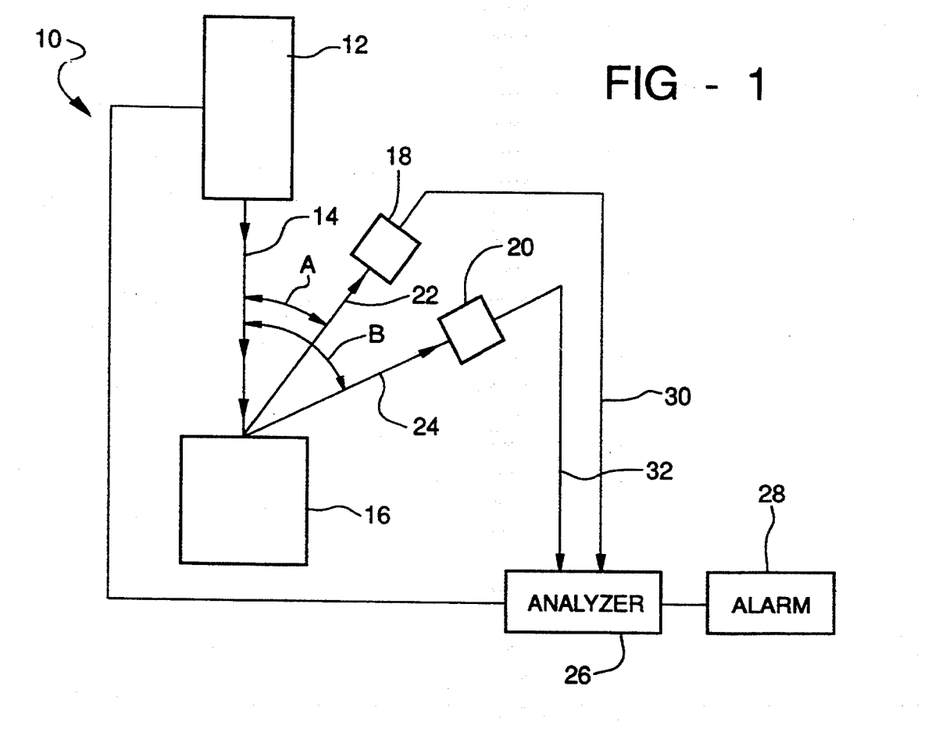
FIG. 1 is a schematic depiction of one analytical system structured in accord with the principles of the present invention.

The present invention provides a neutron resonant scatter analysis system which requires only a single monoenergetic neutron beam for its operation. The invention relies upon the anisotropic nature of the elastic scattering of particular energies of neutrons by particular nuclei. FIG. 1 depicts an apparatus 10 structured in accord with the principles of the present invention. The apparatus includes a neutron source 12 operable to impinge a monoenergetic beam of neutrons 14 onto an object 16 being interrogated. The depicted system includes two neutron detectors 18, 20. The first detector 18 is disposed to detect neutrons 22 scattered through a first scattering angle A. The second detector 20 is disposed to detect a second group of neutrons 24 scattered through a second scattering angle B. The detectors 18, 20 are each in communication with an analyzer 26 which has an alarm 28 associated therewith.

The neutron source 12 is operative to provide a monoenergetic beam of neutrons 14 and to direct that beam to the object 16. Within the context of the present invention, a monoenergetic neutron beam is defined as a beam having a relatively narrow distribution of energies, analogous to a beam of light of a single nominal wavelength. As such, the beam may also be referred to as monochromatic. It is to be understood that in a typical system a gaussian distribution of neutron beam energies is typically encountered, and for that reason a monoenergetic beam may include some neutrons having energies slightly higher or slightly lower than the nominal beam energy. There are a variety of neutron sources well known in the art. As noted above, neutrons may be readily generated by bombarding a target nucleus such as lithium, deuterium or the like with an ionized beam of another material typically hydrogen or deuterium. Other materials such as carbon, oxygen, tritium and helium may be similarly employed, either in the form of pure materials or as compounds thereof. The energy of the emitted neutrons will be a function of the energy of the ions and the nature of the target nucleus; and, by control of these parameters, the energy of the neutron beam may be selected. As is well known in the art, the neutron source 12 may include a collimator (not shown) which functions to define a parallel neutron beam. The collimator may comprise a relatively thick body of neutron absorbing material, such as polyethylene loaded with boron, having a plurality of elongated channels therethrough. The channels function to permit only those neutrons traveling in approximately parallel paths to pass.

The neutron detectors 18, 20 may comprise scintillation type detectors as are well known to those of skill in the art. One detector having particular utility in the present invention is a resonance enhanced neutron detector disclosed in U.S. Pat. No. 5,142,153, the disclosure of which is incorporated herein by reference. As is well known in the art, the detectors 18, 20 may include appropriately placed neutron shields to prevent spurious readings.

In operation, the neutron source 12 is activated so as to provide a monoenergetic beam of neutrons 14 having an energy which is selected to produce anisotropic resonant scattering from a material of interest in the object 16. In general, the neutrons are elastically scattered from a nucleus through a large number of different angles; however, the scattering cross section of the nucleus (i.e., the probability of an interaction leading to scattering) is greater for neutrons scattered through particular angles. In accord with the present invention, the first detector 18 is disposed at a first scattering angle A (said angle being defined herein as being measured from the incident neutron beam 14) at which resonant scattering by the preselected element is expected to occur. The second detector 20 is disposed at a second angle B at which no resonant scattering by the preselected species, or any expected competing species, will occur.

The detectors 18, 20 each produce a signal in response to the impact of a neutron thereupon and this signal is communicated to an analyzer 26 by lines 30 and 32 respectively. The analyzer compares the signal from the first detector 18 and the second detector 20 to determine if resonant scattering has occurred. The analyzer may simply comprise a comparator circuit which measures the relative strength of the signals from each of the detectors. If the signal from the first detector 18 is of increased strength relative to the signal from the second detector 20 it is assumed that resonant scattering occurred and that the preselected nucleus is present in the object 16. The analyzer may simply determine the difference of the two signals, which difference may then be interpreted to determine the presence or absence of the species of interest. In other instances, the analyzer may include further processing circuitry, such as a relay circuit operative to sound an alarm 28. In general, the strength of the signal from the detectors 18, 20 will be proportional to the intensity of the neutrons. As such, the system may operate, after calibration, to provide a quantitative indication of the amount of the species of interest in the object 16.

The choice of beam energy and detector placement will depend upon the specific element which is being analyzed for. The combination may be determined experimentally by measuring the positional dependence of the scattering cross section of particular elements, at neutron energies of interest. In some instances, reference may be made to published neutron scattering data.

In some instances, the neutron source 12 will operate in a pulsed mode so as to generate a pulsed beam of neutrons. The detectors 18, 20 and/or the analyzer 26 are operated in synchrony with the neutron source, on a time-of-flight basis so as to only detect scattered neutrons resultant from the pulses. This mode of operation will minimize stray noise and improve the accuracy and the technique.

Figure 3A:
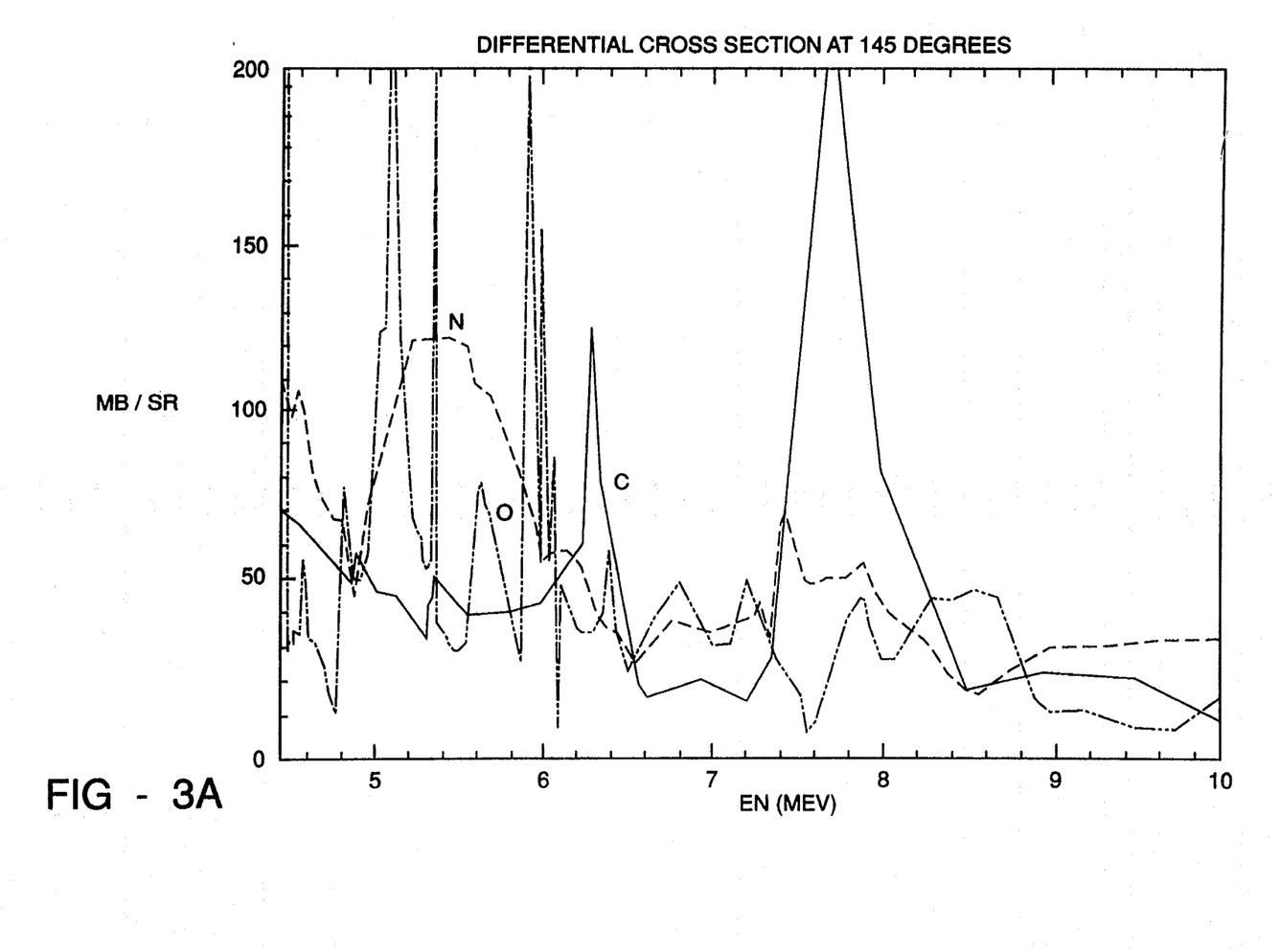
FIG. 3A is a graph depicting the neutron scattering cross section of oxygen, nitrogen and carbon at 145 degrees as a function of the energy of the incident neutrons.
Figure 3B:
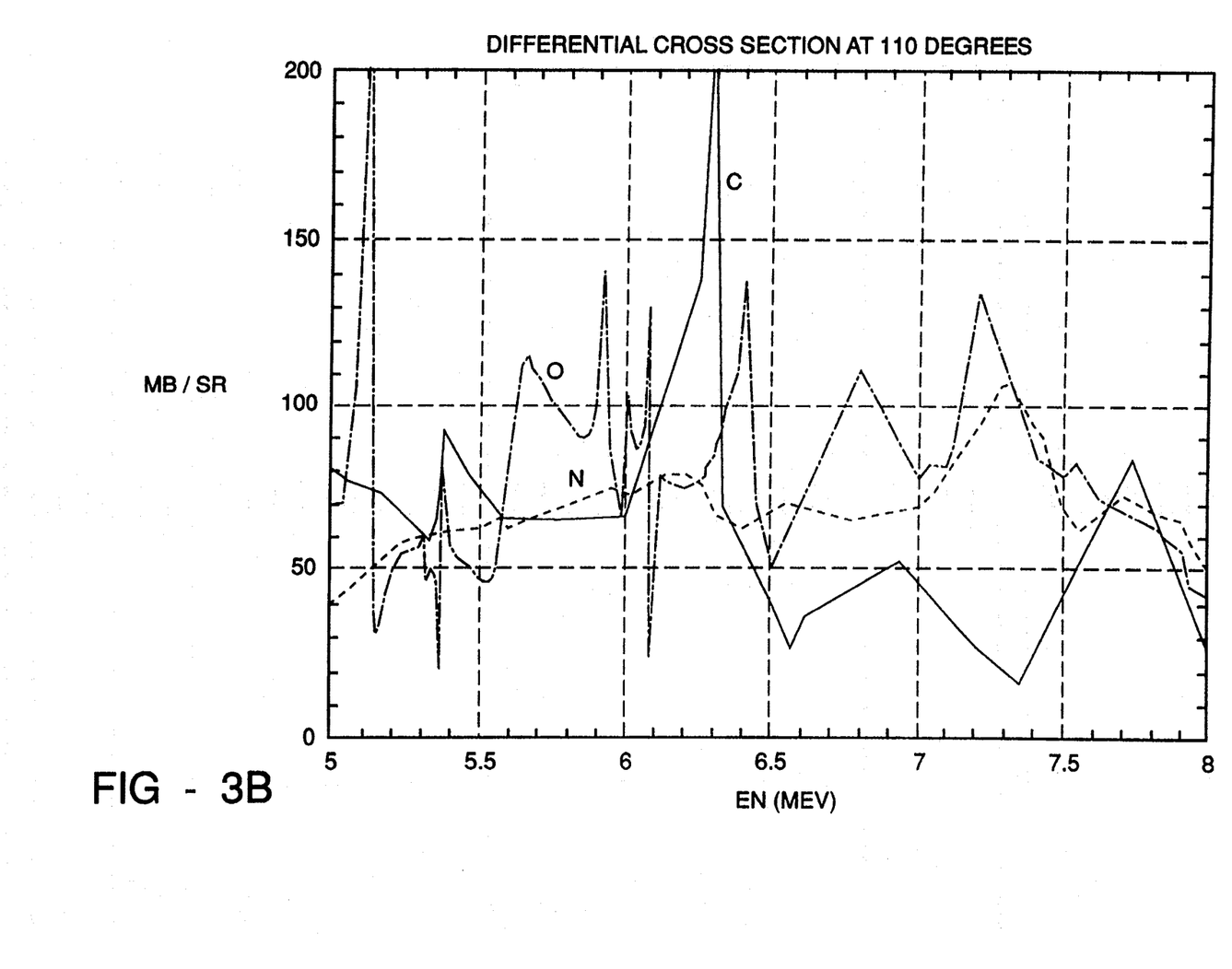
FIG. 3B is a graph of the neutron scattering cross section of oxygen, nitrogen and carbon at 110 degrees as a function of the energy of the incident neutrons.

Referring now to FIGS. 3A and 3B, there are shown a set of graphs depicting the scattering cross section, in millibarns per steradian, for oxygen$^{16}$, nitrogen$^{14}$, and carbon$^{12}$, as a function of incident neutron energy. FIG. 3A depicts scattering data measured at 145 degrees, and FIG. 3B depicts data measured at 110 degrees. It will be seen that there is a strong dependence of the scattering cross section on both neutron energy and scattering angle. It will be observed that over the energy range of 5.2 to 5.6 MeV neutrons are strongly scattered from nitrogen at 145°. It will also be noted that oxygen and carbon have a relatively low scattering cross section for 5.4 MeV neutrons at 145°. Referring now to FIG. 3B, it will be seen that 5.4 MeV neutrons are much more weakly scattered by nitrogen at an angle of 110° as compared to an angle of 145°; also, the scattering cross sections of carbon and oxygen are low for 5.4 MeV neutrons at 110°. In accord with the present invention, these difference in scattering cross section of the nuclei may form the basis of an analytical system.

One embodiment of a system, generally similar to that of FIG. 1, operative to measure nitrogen in the presence of oxygen and carbon, includes a neutron source 12 operative to provide a monoenergetic beam of neutrons having an energy in the range of 5.3 to 5.6 MeV, a first detector 18 disposed at a scattering angle in the range of approximately 140° to 150° and a second detector 20 at an angle in the range of approximately 105° to 115°. It is to be appreciated that in some instances competing resonances may require that the element of interest be measured at a point slightly off peak resonance in order to avoid interference from other species and such geometries are also in the scope of the present invention.

Figure 4:
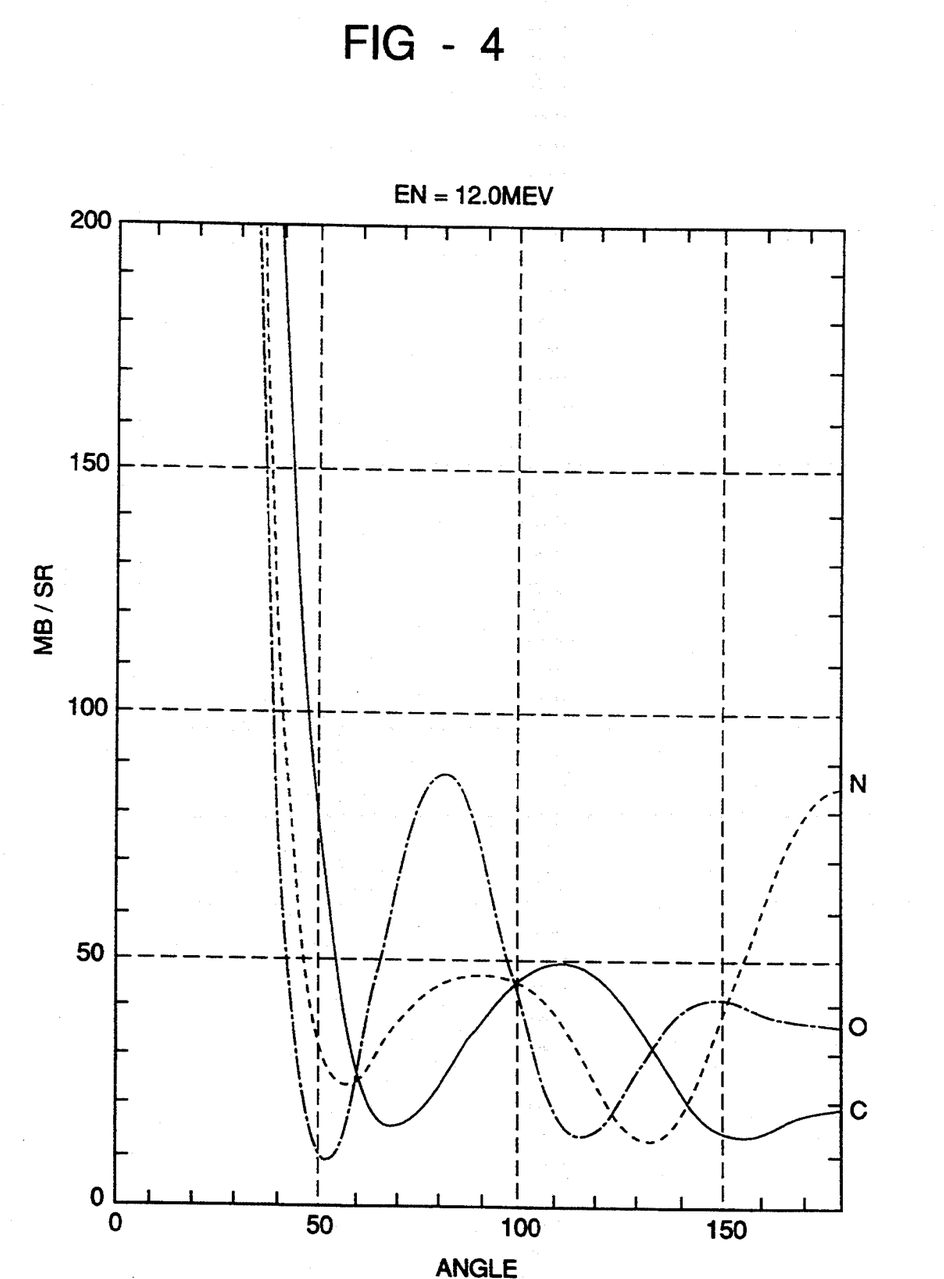
FIG. 4 is a graph depicting the positional dependence of the scattering cross section of oxygen, nitrogen and carbon for 12.0 MeV neutrons.

As noted above, the characteristics of the scattering vary as the neutron beam energy and detector position are varied. FIG. 4 depicts the scattering cross section of carbon oxygen and nitrogen for 12.0 MeV neutrons, and it will be noted that peak positions have changed significantly as compared to data presented in FIG. 5 and in FIGS. 3A and 3B.

In some instances there are particular advantages to employing a side scatter system, that is a system which detects neutrons elastically scattered through an angle of approximately 90°. A system of this type provides a simple geometry compatible with high volume automated scanning systems. Also, in some instances, the scattering cross section of a particular element, with regard to side scattered neutrons, is much higher than that of a second element, and this phenomenon may be used to further enhance the sensitivity of the technique of the present invention. As shown in FIG. 3B, nitrogen exhibits a strong resonant scattering for 7.3 MeV neutrons at 110° (approximately 105 MB/SR). Carbon, in contrast, has a low scattering cross section (approximately 20 MB/SR) for 7.3 MeV neutrons at this angle. Therefore, a side scatter system could be easily implemented to measure nitrogen in the presence of carbon, by disposing one detector at 110° and another at a different angle where neither carbon nor nitrogen manifests resonant scattering.

Figure 5:
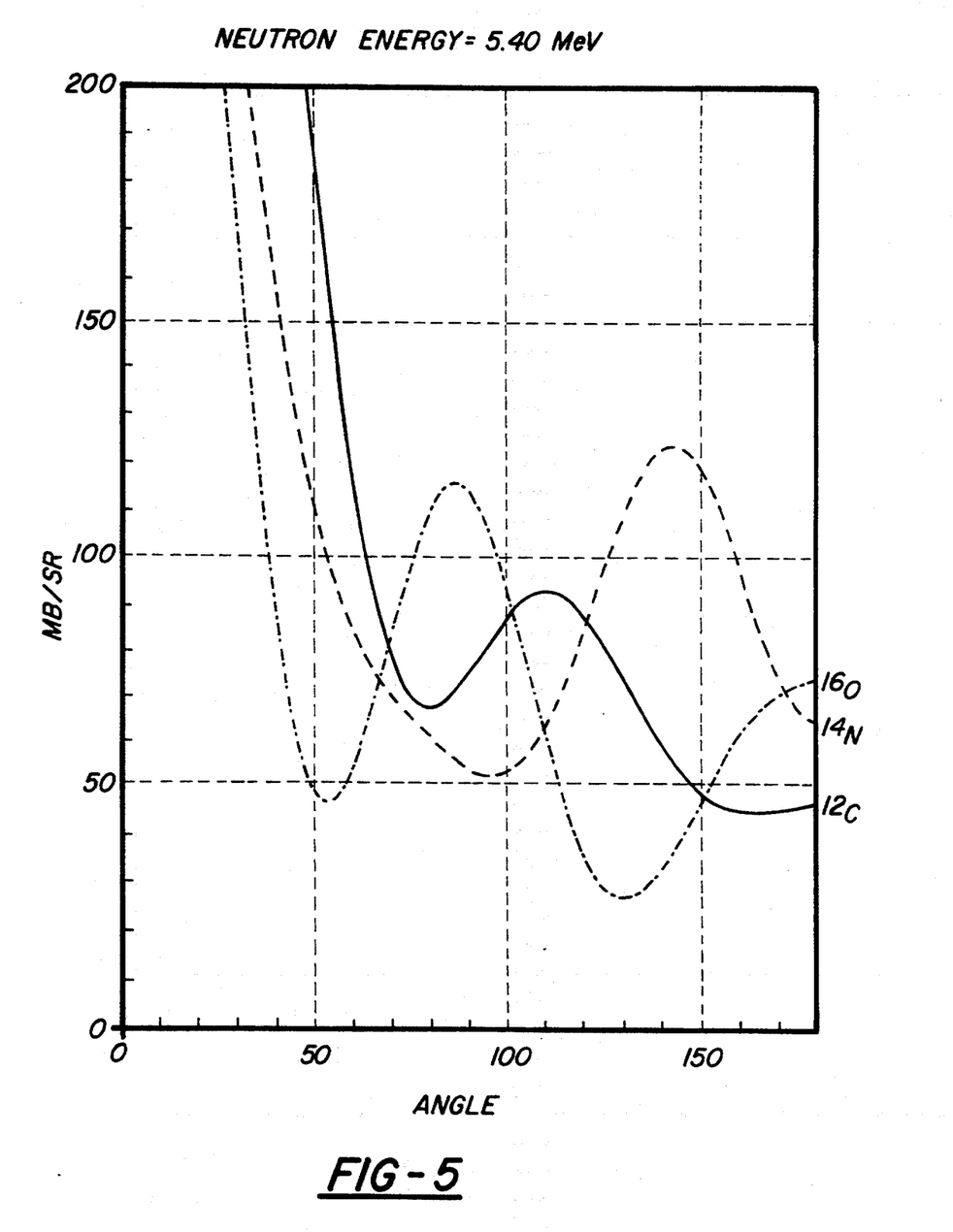
FIG. 5 is a graph depicting the positional dependence of the scattering cross-section of oxygen, nitrogen and carbon for 5.40 MeV neutrons.

FIG. 5 depicts the angular dependence of the scattering cross sections of oxygen[16], nitrogen[14] and carbon[12] for 5.4 MeV neutrons. It will be noted that while nitrogen has a peak centered at 145°, this peak is fairly broad, and has a large value over the range of approximately 130° K. to 160°. Also, it will be noted that over this range carbon and oxygen have lower scattering cross sections. Over the angular range of 140° to 150°, the nitrogen signal is quite strong compared to the carbon and oxygen signals. Over the angular range of 105° to 115° the nitrogen and oxygen scattering cross-sections are low. It will thus be seen that there are practical ranges of energies and positions which correspond to the various nominal resonance positions and energies, and the invention may be practiced within these ranges as well as at the precise resonance maxima.

Figure 2:
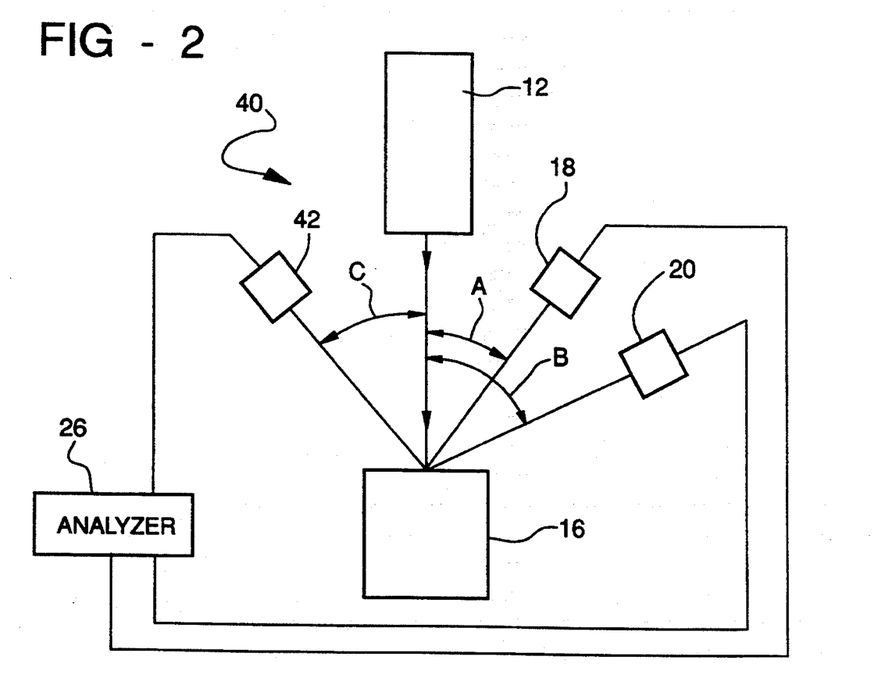
FIG. 2 is a schematic depiction of another analytical system structured in accord with the principles of the present invention.

It will be appreciated that the system described in FIG. 1 may be further modified to simultaneously determine the presence of two or more preselected elements by the inclusion of more detectors. Depicted in FIG. 2 is another system 40 structured in accord with the principles of the present invention. The system 40 of FIG. 2 is generally similar to that of FIG. 1 insofar as it includes a source of monoenergetic neutrons 12, a first detector 18, a second detector 20 and an analyzer 26. The system 40 of FIG. 2 further includes a third detector 42 disposed at a third scattering angle C. The scattering angle C is selected to correspond to the angle at which resonant scattering occurs from the second element of interest. The angle C is selected to assure that resonant scattering from the second nucleus of interest will be observed and to further assure that no resonant scattering from other species in the object 16 will be encountered. In this embodiment, the second detector 20 also serves as non-resonant reference for the second species. In other embodiments, a separate detector may serve this function. Clearly, it will be appreciated that still further elements may be analyzed by the addition of further detectors. In the FIG. 2 embodiment, the analyzer 26 operates to determine whether a resonant signal is measured by the first 18, or third 42 detector, as in the FIG. 1 example. The analyzer may further include a signal processor, such as a programmed microcomputer, which will determine the relative ratio of the elements measured by the first 18 and third 42 detectors. In this manner particular classes of materials, such as narcotics, explosives and the like may be detected.

While the foregoing has primarily been described with reference to the detection of nitrogen, oxygen and carbon, and in the general context systems for of detecting explosives or narcotics; it will be understood that the principles of the present invention may be extended to other types of analysis and detection system. The system may be configured to detect beryllium, deuterium, tritium and other such materials characteristic of nuclear devices. The system may also be configured to perform non-destructive testing, for example on metallurgical samples, polymeric materials and the like, by the appropriate choice of neutron source and detector placement. These and other variations of the present invention will be readily apparent to those of skill in the art from the drawings, discussion and descriptions herein. Accordingly, it is to be appreciated that the foregoing, is merely illustrative of particular embodiments of the present invention, and is not meant to be a limitation upon the practice thereof. It is the following claims, including all equivalents, which define the scope of the invention.

I claim:

1. An apparatus for the non-invasive inspection of an object to determine the presence of at least one preselected element therein, said apparatus comprising:
   a neutron source operative to provide a monoenergetic beam of neutrons and to direct said beam onto said object, said neutrons being of a preselected energy such that they are anisotropically scattered from said preselected element so as to provide a resonantly scattered group of neutrons at a first scattering angle and a non-resonantly scattered group of neutrons at a second scattering angle;
   a first neutron detector disposed at a location corresponding to said first scattering angle, and operative to detect said resonantly scattered neutrons and provide a first signal corresponding thereto;
   a second neutron detector disposed at a location corresponding to said second scattering angle, and operative to detect said non-resonantly scattered neutrons and provide a second signal corresponding thereto; and
   an analyzer operative to receive said first and second signals and compare said first and second signals so as to determine if said resonantly scattered neutrons are present; whereby, the presence of said resonantly scattered neutrons indicates the presence of said preselected element in said object.

2. An apparatus as in claim 1, wherein said analyzer is further operative to activate an alarm signal if it determines that said resonantly scattered neutrons are present.

3. An apparatus as in claim 1, wherein said first and second neutron detectors are each operative to provide a signal corresponding to the number of neutrons detected thereby.

4. An apparatus as in claim 1, further operative to determine the presence of said at least one preselected element in an object in the presence of a second element therein, wherein said neutron source is operative to provide a monoenergetic beam of neutrons having a preselected energy such that no resonant scattering of said neutrons, by said second element occurs at said first scattering angle and at said second scattering angle.

5. An apparatus as in claim 4, wherein said neutron source is further operative to provide a monoenergetic beam of neutrons having a preselected energy such that said neutrons are anisotropically scattered from said second element so as to provide a resonantly scattered group of neutrons at a third scattering angle; said apparatus further including a third neutron detector disposed in a location corresponding to said third scattering angle, and operative to detect the neutrons resonantly scattered from said second element and to provide a third signal corresponding thereto;
   wherein said analyzer is further operative to receive said third signal and to compare said first, second and third signals so as to further determine if neutrons resonantly scattered from said second element are present.

6. An apparatus as in claim 1, wherein nitrogen is said preselected element in the object, and wherein said object further includes carbon and oxygen and wherein said neutron source is operative to provide a monoenergetic beam of neutrons having an energy in the range of 5.3 to 5.6 MeV and wherein said first scattering angle is in the range of 140° to 150° and said second scattering angle is in the range of 105° to 115°.

7. An apparatus as in claim 1, wherein said neutron source is operative to provide pulses of neutrons and wherein said analyzer is operative, on a time of flight basis, to analyze only those signals corresponding to said pulses of neutrons.

8. A method for the non-invasive inspection of an object to determine the presence of at least one preselected element therein, said method comprising:

provided a neutron source operative to generate a monoenergetic beam of neutrons having a preselected energy such that said neutrons are anisotropically scattered from said preselected element so as to provide a resonantly scattered group of neutrons at a first scattering angle and a non-resonantly scattered group of neutrons at a second scattering angle;

directing said monoenergetic beam of neutrons onto said object;

disposing a first neutron detector in a location corresponding to said first scattering angle, said detector operative to detect neutrons impinging thereupon and to provide a first signal corresponding thereto;

disposing a second neutron detector in a location corresponding to said second scattering angle, said second detector operative to detect neutrons impinging thereupon and to provide a second signal corresponding thereto; and comparing said first and second signals so as to determine if said resonantly scattered neutrons are present; whereby the presence of said resonantly scattered neutrons indicates the presence of said preselected element in said object.

* * * * *